(12) United States Patent
Kandler et al.

(10) Patent No.: US 6,326,197 B1
(45) Date of Patent: *Dec. 4, 2001

(54) PLATELET SUSPENSIONS AND METHODS FOR RESUSPENDING PLATELETS

(75) Inventors: Richard L. Kandler, McHenry; Liam C. Farrell, Palatine, both of IL (US)

(73) Assignee: Baxter International Inc., Deerfield, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/490,191

(22) Filed: Jan. 24, 2000

Related U.S. Application Data

(63) Continuation of application No. 08/871,115, filed on Jun. 9, 1997, now Pat. No. 6,063,624.

(51) Int. Cl.⁷ .............................. C12N 5/08; A01N 1/02
(52) U.S. Cl. .................................. 435/372; 435/2
(58) Field of Search ........................................ 435/372, 2

(56) References Cited

U.S. PATENT DOCUMENTS

| Re. 32,874 | 2/1989 | Rock et al. | 424/101 |
|---|---|---|---|
| 5,411,983 | 5/1995 | Wissner et al. | 514/398 |
| 5,462,752 | 10/1995 | Chao et al. | 424/532 |
| 5,622,867 | 4/1997 | Livesey et al. | 436/18 |

OTHER PUBLICATIONS

H. Gulliksson, et al., "Storage of platelets in additive solutions: a new method for storage using sodium chloride solution," Transfusion 1992; 32:435–440.

H. Gulliksson, "Storage of platelets in additive solutions: the effect of citrate and acetate in in vitro studies," Transfusion 1993; 33:301–303.

J. Connor, et al., "Recovery of in vitro functional activity of platelet concentrates stored at 4 degrees C and treated with second–messenger effectors," Transfusion 1996: 36:691–698.

Zucker et al., Thrombos. Haemostas. (Stuttg.), 42(3), "Hypertonic Solutions Decrease Light Transmission of Platelet Suspensions," pp. 1062–1063 (1979).

Wallvik et al., Vox Sang., 58(1), "The Platelet Storage Capability of Different Plastic Containers," pp. 40–44 (1990).

Eriksson et al., Vox Sang., 59(3), "Platelet Concentrates in an Additive Solution Prepared from Pooled Buffy Coats," pp. 140–145 (1990).

Gulliksson et al., Vox Sang., 61(3), "Storage of Platelets in a New Plastic Container, " pp. 165–170 (1991).

Hess et al., J. Trauma, 32(1), "Effects of 7.5% NaCl/6% Dextran 70 on Coagulation and Platelet Aggregation in Humans," pp. 40–44 (1992).

*Primary Examiner*—Jon P. Weber
(74) *Attorney, Agent, or Firm*—Andrew G. Kolomayets; Michael C. Mayo; Bradford R. L. Price

(57) ABSTRACT

Platelet suspensions and methods for resuspending platelet concentrates are disclosed. The platelet concentrates are resuspended by combining a platelet concentrate with a substance capable of resuspending platelets, such as a salt solution. The resuspended platelets may be stored and/or administered to a patient.

13 Claims, No Drawings

PLATELET SUSPENSIONS AND METHODS FOR RESUSPENDING PLATELETS

This is a continuation of prior application Ser. No. 08/871,115, filed Jun. 9, 1997, now U.S. Pat. No. 6,063,624.

The present invention generally relates to the resuspension of blood platelets and/or platelet concentrates after separation of the platelets or platelet concentrate from the blood of a donor. More specifically, the present invention concerns platelet suspensions, media in which platelets may be resuspended, the suspension of platelets in such media, and methods for obtaining or preparing such suspensions.

BACKGROUND

Whole blood is made up of various cellular components such as red cells, white cells and platelets suspended in its liquid component, plasma. Whole blood can be separated into its constituent components (cellular or liquid), and the separated component can be administered to a patient in need of that particular component. For example, platelets can be removed from the whole blood of a healthy donor, collected, and later administered to a cancer patient, whose ability to make platelets has been destroyed by chemotherapy or radiation treatment.

Most commonly, platelets are collected by continuously or intermittently introducing whole blood from a donor into a centrifuge chamber wherein the whole blood is separated into its constituent components, including platelets, based on the densities of the different components. In the separation of platelets, sometimes referred to as plateletpheresis, the platelets are often concentrated to form a layer of packed platelets with some residual plasma (hereinafter "platelet concentrate"). For storage and/or transfusion to the patient, however, the platelet concentrate must be resuspended in a liquid medium, such as plasma.

There are several commercially available devices useful in the separation and collection of platelets. One such device is the CS-3000® Plus Blood Cell Separator, made by Baxter Healthcare Corporation of Deerfield, Ill. The Baxter CS-3000® Plus is an automated continuous flow centrifuge capable of performing numerous blood separation procedures, including plateletpheresis.

In a plateletpheresis procedure on the CS-3000® Plus, platelets are separated from whole blood in two "stages". In a first stage, red blood cells and white blood cells are separated from platelets and plasma. The separated red blood cells and white blood cells are returned to the donor and the platelets and plasma ("platelet-rich plasma") proceed to the second stage for further processing. In a second stage, the platelet-rich plasma is separated into plasma depleted of platelets (platelet-poor plasma) and a platelet concentrate, which as defined above, includes platelets and residual plasma. Most of the plasma is returned to the donor, but some remains with the platelet concentrate. At the completion of the platelet collection, the platelet concentrate is then resuspended by mixing the platelet concentrate with an additional amount of plasma. After the platelets have resuspended, they may be transfused to a patient.

Another device useful in plateletpheresis is the AMICUS™ Separator—also an automated continuous flow blood cell separator made by Baxter Healthcare Corporation. In the AMICUS™, red blood cells and white blood cells are also separated from platelet-rich plasma in a first stage and the platelet-rich plasma is then separated into platelet poor plasma and platelet concentrate in a second stage. The collected platelet concentrate is also resuspended in additional plasma.

In addition to the automated procedures described above, platelets can also be collected on systems where the donor is not connected to the instrument during the plateletpheresis procedure. In these "manual" systems, whole blood is collected from a donor. The container of collected whole blood is then centrifuged to separate the platelet rich plasma in a first stage from the other components. In a second stage of the procedure, platelets are separated from plasma to form a platelet concentrate. The platelet concentrate is then resuspended in a liquid, such as plasma.

Although plasma is effective for resuspending platelets, it may not be the ideal medium for platelet resuspension for several reasons. First, plasma itself is a valuable blood component that can be used or further processed for use in the treatment of patients with other disorders. Thus, it would be desirable to save the plasma for end uses other than platelet resuspension. Second, platelets often do not completely resuspend in plasma and/or complete resuspension of platelets in plasma occurs over an extended period of time.

Platelets that have not completely resuspended may be unsuitable for further processing or transfusion because of the presence of platelet aggregates (i.e. clumps of platelets). Platelet aggregates are undesirable because they can clog transfusion filters commonly used in platelet transfusions and/or platelet processing, such as filters designed for removal of white cells. Lower throughput because of clogged filters results in fewer platelets administered to a patient.

It is known, for example, that platelets will resuspend in saline solution (0.9% NaCl) and saline has been used to resuspend platelets in platelet washing procedures as shown and described in U.S. Pat. No. 5,462,752. Solutions that are primarily intended for the storage of platelets may also be useful for resuspending platelets. For example, the Platelet Additive Solutions (PAS) made by Baxter Healthcare Corporation are used for long term storage of platelets, but also may assist in the suspension of platelets. However, in addition to sodium chloride, these solutions include other components designed to help preserve the platelets such as (in the case of PAS I) sodium citrate, mannitol, phosphate, potassium chloride, See Eriksson, "Platelet concentrates in an Additive Solution Prepared from Pooled Buffy Coats," Vox Sang 1990:59:140–145 (1990) and (in the case of PAS II and PAS III) sodium acetate which serves as a nutrient for platelets. Thus, it would be desirable to resuspend platelet concentrates as completely as possible and in as short a time period as possible in a solution other than plasma or a platelet storage medium, and still provide a suspension of platelets suitable for storage or, if desired, readily available for transfusion to a patient.

SUMMARY OF THE CLAIMED INVENTION

In one aspect, the present invention is directed to a suspension of platelets that includes a platelet concentrate that is suitable for administration to a patient, a salt solution, and is substantially free of platelet aggregates.

The present invention is also directed to the method for providing a suspension of platelets. The method includes providing a quantity of whole blood and separating the platelets from the whole blood, concentrating the platelets, and resuspending the platelet concentrate. The method may further include administering the platelet suspension to a patient.

DETAILED DESCRIPTION OF THE DISCLOSED EMBODIMENTS

A more detailed description of the platelet suspensions made in accordance with the present invention and the methods for providing such platelet suspensions is set forth below. It should be understood that the description below is intended to set forth one or more embodiments of the present invention, and is not intended to set forth all possible variations or applications of the present invention. For this reason, the scope of the invention is not defined by or limited to the embodiments described below, but includes future variations or embodiments not presently appreciated by the inventors.

Platelet concentrates can be obtained by any known techniques. For example, platelet concentrates can be prepared by separating whole blood into its components, including platelet concentrates, using an automated cell separator such as the CS-3000® Plus, AMICUS™, other devices, and/or manual blood collection systems.

In the Baxter CS-3000® Plus, as described generally in U.S. Pat. No. 4,146,172 which is assigned to the assignee of the present application and is incorporated by reference herein, anticoagulated whole blood is introduced into a separation chamber within a rotating centrifuge (spinning at approximately 1600 rpm). In the separation chamber, anticoagulated whole blood is separated into red and white cells on the one hand and platelet-rich plasma on the other hand. The platelet-rich plasma is then pumped from the separation chamber into a second collection chamber within the rotating centrifuge. There the platelet-rich plasma is separated into platelet poor plasma and platelet concentrate.

The platelet collection procedure results in a platelet concentrate (as defined above) having a volume of anywhere between 5–150 ml, depending on the volume of the collection chamber. The number of platelets collected is typically between 3 to $12=10^{11}$ platelets. Once the platelet concentrate has been collected, the platelet concentrate is resuspended in the manner described below and transferred, in a sterile manner, from the container within the collection chamber to a storage container.

In the AMICUS™ Separator, as described generally in U.S. Pat. No. 5,529,691, which is also incorporated by reference herein, anticoagulated whole blood is introduced into a rotating centrifuge (spinning at approximately 3200 rpm) and is separated (in a first stage) into red and white blood cells on the one hand and platelet-rich plasma on the other hand. The platelet-rich plasma is further separated (in a second stage) into platelet poor plasma and platelet concentrate. The final volume of the platelet concentrate is approximately 5–35 ml (which, as described above, includes a portion that is platelets and the remainder of which is plasma). The number of platelets collected is typically between 3 to $12 \times 10^{11}$ platelets, and more typically, approximately $4 \times 10^{11}$ platelets.

Prior to the present invention, the collected platelet concentrate was typically resuspended in a large volume of plasma. For example, platelet concentrate collected on the AMICUS™ is typically resuspended in at least 150 ml of plasma. (The volume of plasma needed for resuspension will depend on the number of platelets collected i.e. platelet yield). However, in accordance with the present invention, no additional plasma (i.e. beyond the plasma which is part of the platelet concentrate) is needed for the resuspension of platelets. In accordance with the present invention, the platelet concentrate is combined with a substance capable of resuspending the platelet concentrate. The substance can be a solid powder (such as, but not limited to, NaCl or KCl), a suspension or a solution, such as a salt solution. In the case of a salt solution, anywhere between 5–500 ml of the solution may be combined with the platelet concentrate to resuspend the platelet concentrate. More typically, the volume of the solution is between 20–40 ml. The volume of solution needed to resuspend the platelets will depend on the number of platelets collected. The container of platelet concentrate and resuspension solution may be shaken or otherwise agitated to assist in resuspension.

In accordance with the present invention, it has been discovered that solutions suitable for resuspension of platelets include several salt solutions such as sodium chloride (NaCl) and potassium chloride (KCl). Typically, the concentration of salt in the solution is approximately 0.9% A 0.9% sodium chloride solution and 1.12% potassium chloride solution are suitable for resuspending platelets. It has also been discovered that hypertonic solutions (i.e. solutions having an osmolality greater than 0.9% NaCl) are useful in the resuspension of platelets. For example, and as described in more detail below, 1.8% NaCl solutions are also effective in quickly and efficiently resuspending the platelet concentrate. Similarly, a 2.24% KCl solution has also been shown to be effective for resuspending platelets. Other variants of the above-identified solutions are also suitable, such as a 0.9% sodium chloride solution with amiloride or a 1.8% sodium chloride solution with amiloride. Still other concentrations of the sodium chloride and potassium chloride solutions are also possible, such as concentrations between 0.45%–3.0%.

Thus, the final platelet suspension includes anywhere between 5–150 ml of platelet concentrate, and more typically approximately 30–35 ml of platelet concentrate (as defined above) and approximately 5–500 ml, and more typically 20–30 ml of the salt solution used for resuspension. Platelets resuspended in the salt solutions may be suitable for transfusion soon after resuspension and, in any event, in less than 24 hours. If the platelets are not to be transfused immediately, and storage of the platelets is required, the platelet concentrate and salt solution may be further combined with a quantity of plasma and/or a platelet storage medium.

It should be understood that for the platelet suspensions to be suitable for transfusion to a patient, the suspension should be substantially isotonic (i.e. where the osmotic pressure outside the platelet cell is substantially equal to the osmotic pressure inside the cell). Thus, combining the platelet concentrate with 0.9% NaCl, which is an isotonic solution, does not significantly affect the osmolality of the suspension and, therefore the suspension may be suitable for transfusion to a patient. If the platelet concentrate is combined with a hypertonic solution, such as a 1.8% NaCl, further dilution of the suspension may be required before the suspension can be administered to a patient.

Several tests were conducted to determine the degree and speed of platelet resuspension in different salt solutions as compared to plasma. For purposes of these tests, the platelets were collected from different donors A–G on either the AMICUS™ (donors A,B,C,D,F,G and H) or the CS-3000® Plus (donor E)in the manner described above. The collected platelet concentrates were resuspended in plasma and stored at 20–24° centigrade and were 4–6 days old when tested. Platelet samples from those platelet resuspensions were prepared in the manner described below. The test solutions used were plasma, Thrombosol®, Platelet Additive Solution III (PAS III), and the salt solutions 0.9% saline, 0.45 sodium chloride, 0.45 sodium chloride with amiloride, 0.9 sodium chloride with amiloride, 1.8% sodium chloride, 1.8% sodium chloride with amiloride, 0.9% magnesium chloride, and 1.8% magnesium chloride, 1.12% potassium chloride and 2.24% potassium chloride.

The test solutions were either obtained from commercially available sources or prepared from powder. For example, the 0.9% NaCl used is available and was obtained from Baxter Healthcare Corporation of Deerfield, Ill. Other test solutions were prepared from powder in ways that are known to those of skill in the art. (For example 0.9% NaCl can be prepared by dissolving 900 mg of NaCl in approximately 0.1 liter of water to obtain the 0.9% concentrations for the salt solutions. Similarly, the hypertonic NaCl, KCl and MgCl solutions can be prepared by dissolving NaCl, KCl and MgCl in water in ways known to those of skill in the art to arrive at the concentrations set forth in Tables I and II. Thrombosol® is a platelet storage medium available from Lifecell Corporation of The Woodlands, Texas. Thrombosol® includes amiloride, ticlopidine and dipryridamole in DMSO and sodium nitroprusside, adenosine, and heparin in a phosphate buffered saline. A more detailed description of Thrombosol® is set forth in a U.S. Pat. No. 5,622,867. The Thrombosol® solution used in the tests described below was prepared as described in Connor, J. et al. "Recovery of In Vitro Functional Activity of Platelet Concentrates stored at 4° C. and Treated with Second-Messenger Effectors," Transfusion, 1996; 36: 691–698, which is incorporated by reference herein. Finally, PAS III is a platelet storage medium available from Baxter Healthcare Corporation and is manufactured in La Chatre, France. PAS III includes dibasic sodium phosphate, monobasic sodium phosphate, sodium citrate, sodium acetate and sodium chloride.

Vortex Test-time for Total Resuspension

Approximately 4 ml of the platelet suspension (as prepared above) was placed in a clean test tube. The test tube was centrifuged at 3200 rpm for approximately 8 minutes in a Sorval RT 6000 Centrifuge with H1000B rotor to pellet the platelets. The tubes were removed from the centrifuge and all the plasma was removed without disturbing the platelet pellet. Four (4) ml of the test solutions (described above) were individually added to individual tubes without disturbing the pellet and the tube was vortexed in a Vortex Mixer available from Scientific Products (catalog #S8223-1) at high speeds for approximately 15 seconds.

The test was visually assessed for clumps and if clumps remained, the tube was placed on a standard tube rocker and the time was recorded. The tube was monitored until complete resuspension occurred and the time was recorded. As used herein, "complete resuspension" means that no platelet aggregates were visible to the naked eye. The number of minutes for complete resuspension was recorded and the results are reported in Table II.

Aggregometer Test—Percent Resuspension

A second series of tests using the same test solutions was conducted to determine the degree of platelet resuspension in 10 seconds of time. For this test, 0.5 ml of platelet concentrate collected on the AMICUS™ and/or CS-3000® (as described above) was placed in a clean siliconized flat bottom glass Chronolog aggregometer tube. The tube was centrifuged at 3200 rpm for 20 minutes to pellet the platelets. The tube was removed from the centrifuge and all plasma was removed without disturbing the platelet pellet. The test solutions (0.5 ml) (described above) were added and a stir bar was added to the tube. The tube was inserted into a standard blood aggregometer in the platelet-rich plasma area. A baseline absorbance was obtained and the stir bar was switched on to 800 rpm. The absorbance was recorded on a strip chart recorder over time. The recording was allowed to continue until platelet concentrate was completely resuspended.

The strip chart recordings were analyzed by measuring the pen deflection at complete resuspension compared to pen deflection at 10 seconds after the stir bar motor was started. The results in Table I show the percent resuspension in 10 seconds.

TABLE I

[0029]

AGGREGOMETER TESTS

| Aggregometer Test | A | B | C | D | E | F | G | Mean Agg (% resuspension) |
|---|---|---|---|---|---|---|---|---|
| Plasma | 73 | 69 | 88 | 87.8 | 87.8 | 86.5 | 67 | 80 |
| Mean | 87 | 83 | 87.5 | 89.2 | 85.2 | 69.1 | 62 | 9 |
| SD | 90 | 95 | 88.3 | 80.6 | 58.9 | 64.7 | 83 | |
| | 83 | 82 | 88 | 86 | 77 | 73 | 71 | |
| | 9 | 13 | 0 | 5 | 16 | 12 | 11 | |
| Saline | 88 | 90 | 85.1 | 80.9 | 86.3 | 85.2 | 82 | 87 |
| Mean | 96 | 85 | 92 | 87.5 | 79.7 | 78.2 | 92 | 5 |
| SD | 94 | 95 | 92.9 | 89.2 | 78.5 | 88 | 84 | |
| | 93 | 90 | 90 | 86 | 82 | 84 | 86 | |
| | 4 | 5 | 4 | 4 | 4 | 5 | 5 | |
| Thrombosol ® | 92 | 90 | 92.8 | 91 | | 90.8 | 83 | 90 |
| Mean | 86 | 97 | 90.7 | 93.6 | | 87.1 | 85 | 3 |
| SD | 95 | 95 | 90.7 | 88.9 | | 87.2 | 90 | |
| | 91 | 94 | 91 | 91 | | 88 | 86 | |
| | 5 | 4 | 1 | 2 | | 2 | 4 | |
| PAS III | | 91 | | | | | | 89 |
| Mean | 82 | 95 | | | | | | 3 |
| SD | 88 | 95 | | | | | | |
| | 85 | 94 | | | | | | |
| | 4 | 2 | | | | | | |
| 0.45% NaCl | | | 77 | | | | | 82 |
| Mean | | | 86 | | | | | 5 |
| SD | | | 82 | | | | | |
| | | | 82 | | | | | |
| | | | 5 | | | | | |
| 0.45% NaCl w/amilor Mean SD | | | 65 80 84 76 10 | | | | | 76 10 |
| 0.9% NaCl w/amilor Mean SD | | | 86 84 84 85 1 | 85 89 90 88 3 | | | | 86 2 |
| 1.8% NaCl Mean SD | | | 97 96 86 93 6 | 95 95 95 95 0 | | 74 89 94 86 10 | 85 85 91 87 3 | 90 5 |
| 1.8% NaCl w/amilor Mean SD | | | 92 96 94 94 2 | 97 95 84 92 7 | | | | 83 4 |
| MgCl 0.6% Mean SD | | | | | 61 58 58 59 1 | | | 59 1 |
| MgCl 1.2% Mean SD | | | | | 88 69 na 63 8 | | | 63 8 |
| KCl 1.12% | | | | | 88 75 83 82 | 73 83 89 82 | 83 82 83 83 | 82 5 |

TABLE I-continued

AGGREGOMETER TESTS

| Aggregometer Test | A | B | C | D | E | F | G | Mean Agg (% re-suspension) |
|---|---|---|---|---|---|---|---|---|
| | | | | | 6 | 8 | 1 | |
| KCl | | | | | 89 | 92 | 92 | 89 |
| 2.24% | | | | | 88 | 93 | 88 | 3 |
| Mean | | | | | 78 | 92 | 93 | |
| SD | | | | | 85 | 92 | 91 | |
| | | | | | 6 | 0 | 3 | |

TABLE II

VORTEX TEST

| Vortex Test | A | B | C | D | E | F | G | H | Vortex Mean (min) |
|---|---|---|---|---|---|---|---|---|---|
| Plasma | 14.0 | 18.0 | 44.0 | * | 16.0 | 82.0 | 27 | 22.0 | 30.3 |
| Mean | 13.0 | 14.0 | 54.0 | * | 26.0 | 90.0 | * | 30.0 | 11.1 |
| SD | 20.0 | 15.0 | 18.0 | * | 9.0 | 36.0 | * | 24.0 | |
| | 15.7 | 15.7 | 38.7 | | 17.0 | 69.3 | * | 25.3 | |
| | 3.8 | 2.1 | 18.6 | | 8.5 | 29.1 | | 4.2 | |
| Saline | 14.0 | 27.0 | 7.0 | * | 16.0 | * | * | 5.0 | 13.9 |
| Mean | 19.0 | 15.0 | 12.0 | * | 32.0 | * | * | 7.0 | 5.6 |
| SD | 26.0 | 9.0 | 11.0 | * | 5.0 | * | * | 10.0 | |
| | 22.5 | 12.0 | 10.0 | | 17.7 | | | 7.3 | |
| | 4.9 | 4.2 | 2.6 | | 13.6 | | | 2.5 | |
| Thrombosol ® | 7.0 | 6.0 | 68.0 | 13 | | 11.0 | 11 | 5.0 | 15.4 |
| Mean | 13.0 | 15.0 | 31.0 | 18 | | 13.0 | * | 7.0 | 9.8 |
| SD | 7.0 | 3.0 | 12.0 | * | | 23.0 | 10 | 4.0 | |
| | 10.0 | 9.0 | 37.0 | 16 | | 15.7 | 11 | 5.3 | |
| | 4.2 | 8.5 | 28.5 | 3 | | 6.4 | 1 | 1.5 | |
| PAS III | 40.0 | 12.0 | | | | | | | 16.3 |
| Mean | 24.0 | 9.0 | | | | | | | 9.8 |
| SD | 8.0 | 5.0 | | | | | | | |
| | 24.0 | 8.7 | | | | | | | |
| | 16.0 | 3.5 | | | | | | | |
| 0.45% NaCl | | | 78.0 | | | | | | 42.3 |
| Mean | | | 31.0 | | | | | | 31.6 |
| SD | | | 18.0 | | | | | | |
| | | | 42.3 | | | | | | |
| | | | 31.6 | | | | | | |
| 0.45% NaCl w/amilor | | | 56.0 | | | | | | 37.7 |
| Mean | | | 46.0 | | | | | | 23.6 |
| SD | | | 11.0 | | | | | | |
| | | | 37.7 | | | | | | |
| | | | 23.6 | | | | | | |
| 0.9% NaCl (saline) w/amilor | | | 7.0 | | | | | | 14.3 |
| Mean | | | 31.0 | | | | | | 14.5 |
| SD | | | 5.0 | | | | | | |
| | | | 14.3 | | | | | | |
| | | | 14.5 | | | | | | |
| 1.8% NaCl | | | 10.0 | 23 | | 22.0 | 28 | | 21.5 |
| Mean | | | 32.0 | 44 | | 23.0 | 20 | | 6.1 |
| SD | | | 18.0 | 40 | | 24.0 | 19 | | |
| | | | 20.0 | 36 | | 23.0 | 22 | | |
| | | | 11.1 | 11 | | 1.0 | 5 | | |
| 1.8% NaCl w/amilor | | | 10.0 | 23 | | | | | w/amil |
| Mean | | | 3.0 | 44 | | | | | 6.0 |
| | | | 5.0 | 40 | | | | | 3.6 |
| SD | | | 6.0 | 36 | | | | | |
| | | | 3.6 | 11 | | | | | |
| MgCl 0.9% Mean SD | | | | | * | * | | | |
| | | | | | * | * | | | |
| | | | | | * | * | | | |
| MgCl 1.8% | | | | | 16.0 | * | | | 18.7 |
| | | | | | 17.0 | * | | | 3.8 |

TABLE II-continued

VORTEX TEST

| Vortex Test | A | B | C | D | E | F | G | H | Vortex Mean (min) |
|---|---|---|---|---|---|---|---|---|---|
| Mean | | | | | 23.0 | * | | | |
| SD | | | | | 18.7 | | | | |
| | | | | | 3.8 | | | | |
| KCl 1.12 | | | | | 23.0 | * | | | 19.8 |
| Mean | | | | | 10.0 | 23.0 | | | 4.0 |
| SD | | | | | 14.0 | 25.0 | | | |
| | | | | | 15.7 | 24.0 | | | |
| | | | | | 6.7 | 1.4 | | | |
| KCl 2.24 | | | | | 7.0 | 22.0 | | | 15.7 |
| Mean | | | | | 10.0 | 24.0 | | | 2.3 |
| SD | | | | | 5.0 | 26.0 | | | |
| | | | | | 7.3 | 24.0 | | | |
| | | | | | 2.5 | 3.0 | | | |

Table I sets forth the Aggregometer test results for donors A–G. All tests were performed in triplicate and mean values and standard deviations are reported.

Table II sets forth the Vortex test results. "Vortex Mean" values and standard deviations (reported in the last column of Table II) are based on available results obtained for donors A, B, C, E, F and H. Results for donors D and G are not included in the calculation of the "Vortex Mean" and standard deviation reported in the last column of Table II. An "*" indicates that there was no resuspension after 2 hours.

As can be seen, resuspension superior to that of plasma was obtained with several of the solutions tested. For the most part, test solutions that were hypertonic seemed to resuspend the platelets faster and with greater efficiency than plasma or some of the other test solutions.

Based on the foregoing, it is believed that the method of the present invention provides a new, unique, simple and inexpensive method whereby platelets can be completely resuspended and substantially free of aggregates. In addition, use of the alternative, inexpensive salt solutions for platelet resuspension preserves blood plasma for other important end uses.

The above description is intended for illustrative purposes only and is not intended to limit the claims to any of the embodiments described herein. The true scope of the invention is set forth in the appended claims.

What is claimed is:

1. A method for providing a suspension of blood platelets suitable for transfusion to a patient, said method comprising:
    providing a volume of concentrated blood platelets;
    resuspending said platelets in a chloride solution; and
    adding a storage medium different from said chloride solution to said resuspended platelets.

2. The method of claim 1 wherein said chloride solution is selected from the group consisting of 0.9% sodium chloride and 0.9% potassium chloride.

3. The method of claim 1 comprising resuspending said platelets in a hypertonic chloride solution.

4. The method of claim 3 wherein said hypertonic chloride solution is selected from the group consisting of hypertonic sodium chloride and hypertonic potassium chloride.

5. The method of claim 4 wherein said chloride solution comprises 1.8% sodium chloride.

6. The method of claim 5 wherein said chloride solution comprises 1.12% potassium chloride.

7. The method of claim 1 wherein the volume of said concentrated blood platelets is approximately 5–35 ml and the volume of said solution is between approximately 20–40 ml.

8. The method of claim 1 further comprising agitating said platelets and said chloride solution while resuspending.

9. The method of claim 1 wherein said storage medium includes a nutrient.

10. The method of claim 9 wherein said nutrient comprises sodium acetate.

11. A suspension of transfusable blood platelets obtained by (1) providing a platelet concentrate, (2) resuspending said platelet concentrate in a chloride solution, and (3) adding a nutrient containing storage medium to said resuspended platelets wherein said medium is selected from the group consisting of plasma and a platelet storage medium.

12. The suspension of claim 11 wherein said chloride solution is selected from the group consisting of 0.9% sodium chloride and 0.9% potassium chloride.

13. The suspension of claim 11 wherein said chloride solution is selected from the group consisting of hypertonic sodium chloride and hypertonic potassium chloride.

* * * * *